United States Patent [19]

Goralski et al.

[11] 4,052,258

[45] Oct. 4, 1977

[54] DIBROMONITROMETHYL METHYL SULFONE SLIMICIDE

[75] Inventors: Christian T. Goralski; Thomas C. Klingler, both of Midland, Mich.; Paul A. Wolf, Augusta, Ga.

[73] Assignee: The Dow Chemical Company, Midland, Mich.

[21] Appl. No.: 699,547

[22] Filed: June 24, 1976

[51] Int. Cl.$^2$ .......................... D21D 3/00; D21H 5/22
[52] U.S. Cl. .................................. 162/161; 424/337; 71/67
[58] Field of Search .................... 424/337; 162/161; 71/67

[56] References Cited

U.S. PATENT DOCUMENTS

| 3,338,779 | 8/1967 | Herschler et al. | 424/337 |
| 3,426,134 | 2/1969 | Shema et al. | 424/337 |
| 3,882,247 | 5/1975 | Bullock | 424/337 |
| 3,930,015 | 12/1975 | Swered et al. | 162/161 |

OTHER PUBLICATIONS

J. Org. Chem. (1969) vol. 34, pp. 3104–3107.

*Primary Examiner*—Delbert R. Phillips
*Attorney, Agent, or Firm*—Theodore Post; C. Kenneth Bjork

[57] ABSTRACT

Dibromonitromethyl methyl sulfone is effective as a slimicide at a concentration of about 100 parts per million.

3 Claims, No Drawings

DIBROMONITROMETHYL METHYL SULFONE SLIMICIDE

SUMMARY OF THE INVENTION

This invention concerns the use of dibromonitromethyl methyl sulfone as a slime control agent. The compound is useful at concentrations approximating 100 parts per million (hereinafter ppm) at a pH of about 5 to about 7. The compound is used in an aqueous medium which contains a minimum amount of an organic solvent such as, for example, acetone, dimethylformamide (hereinafter DMF) or a glycol ether such as, for example, propylene glycol methyl ether, commercially available as Dowanol(®) PM glycol ether. A stock aqueous solution, for example, containing 0.1 percent of the test compound is conveniently prepared containing a minimum solubilizing amount of acetone, DMF or Dowanol(®) PM as solvent. The compound is effective in areas which are subject to slime formation. Among these, an important use is in and about pulp and paper mills.

DESCRIPTION OF THE PREFERRED EMBODIMENTS

The following additional description and examples further describe the invention and the manner and process of making and using it to enable the art skilled to make and use the same and set forth the best mode contemplated by the inventors of carrying out the invention.

EXAMPLE 1

Use of Dibromonitromethyl Methyl Sulfone as a Slime Control Agent

A stock aqueous solution (0.1%) of the compound was prepared using the minimum solubilizing amount of acetone, DMF or Dowanol(®) PM. Required amounts of the stock solution were added to give the final test concentration desired. The substrate tested was an aqueous 0.5% paper pulp suspension buffered at pH 5.2. The inoculum contained 1 ml of the following mixture:

1. Spore culture of *Bacillus subtilis*, ATCC 8473.
2. 24-hour culture of *Aerobacter aerogenes*, ATCC 8308.
3. 24-hour culture of *Candida albicans*, ATCC 10,231.
4. Spore suspension of *Penicillium chrysogenum*, Lever Bros.
5. Spore suspension of *Aspergillus niger*, ATCC 6275.

The mixture was prepared by adding 1 ml of each culture to 95 ml of sterile phosphate buffer. The stock solution and inoculum were added to sufficient volume of 0.5% cellulosic pulp to give a total volume of 100 ml. Sterile cotton swabs dipped into the inoculated pulp were used to streak brain-heart infusion agar plates after 4 and 24 hours of exposure. The plates were read after incubation for 2 days at 37° C for the bacteria and after 5 days at 30° C for the fungi. The inoculum contains a mixture of organisms that are representative of those causing slime in paper mills. Under the above conditions, dibromonitromethyl methyl sulfone gave complete kill of the microorganisms at concentrations of 50 ppm and above.

EXAMPLE 2

Activity of Dibromonitromethyl Methyl Sulfone in Conventional Agar Tests

Dibromonitromethyl methyl sulfone in conventional agar tests gave complete kills of the following microorganisms at 100 ppm:

*P. aeruginosa*
*S. aureus*
*E. coli*
*C. albicans*
*T. mentagrophytes*
*B. subtilis*
*A. aerogenes*
*A. terreus*
*C. pelliculosa*
*P. pullulans* (*Aureobasidium pullulans*)
*S. typhosa*
*Pseudomonas Sp.* Strain 10
*M. phlei*
*R. nigricans*
*Ceratocystis* IPS
*C. fragans*
*Trichoderm Sp.* Madison P-42

Dibromonitromethyl methyl sulfone is prepared by the method of Truce e.a., J. Org. Chem. 34, 3104, 3106, (1969).

What is claimed is:

1. A method for controlling slime-forming organisms by applying to them and to their habitats a cidal amount of a solution containing at least 50 parts per million of dibromonitromethyl methyl sulfone.

2. An aqueous cellulosic pulp containing a slimeicidal amount of at least 50 parts per million of dibromonitromethyl methyl sulfone.

3. A method for controlling bacteria and fungi by applying to them and to their habitats a cidal amount of a solution containing at least 100 parts per million of dibromonitromethyl methyl sulfone.

* * * * *